United States Patent [19]

Sanderson

[11] Patent Number: 5,246,901

[45] Date of Patent: Sep. 21, 1993

[54] POLYSULFONIC ACIDS

[75] Inventor: William A. Sanderson, Menlo Park, Calif.

[73] Assignee: Catalytica, Inc., Mountain View, Calif.

[21] Appl. No.: 197,464

[22] Filed: May 23, 1988

[51] Int. Cl.$^5$ ............................................. B01J 31/00
[52] U.S. Cl. ..................................... 502/162; 502/168; 562/23; 423/10; 534/15; 534/11; 556/18; 556/19; 556/20
[58] Field of Search ............. 562/23; 423/10; 534/11, 534/15; 556/18, 19, 20; 502/162, 168

[56] References Cited

U.S. PATENT DOCUMENTS

| | | | |
|---|---|---|---|
| 2,776,985 | 1/1957 | McKinnis | 260/410.5 |
| 2,799,701 | 7/1957 | Whitehouse et al. | 562/11 |
| 4,235,991 | 11/1980 | DiGiacomo et al. | 556/14 |
| 4,276,410 | 6/1981 | DiGiacomo et al. | 556/14 |
| 4,483,801 | 11/1984 | Sabot | 562/35 |
| 4,483,802 | 11/1984 | Gartner et al. | 562/35 |
| 4,654,176 | 3/1987 | Dang et al. | 562/35 |
| 4,673,535 | 6/1987 | Bahrmann et al. | 562/35 |
| 4,710,321 | 12/1987 | Bahrmann et al. | 562/35 |
| 4,942,218 | 7/1990 | Sanderson et al. | 528/381 |

FOREIGN PATENT DOCUMENTS

WO87/06244 10/1987 PCT Int'l Appl. .

OTHER PUBLICATIONS

CA 51:18004c (1957).
CA 51:8138b (1957).
Gilbert et al., "Sulfonation and Sulfation with Sulfur Trioxide"; Ind. & Eng. Chem., vol. 45, No. 2065 (1953).

Primary Examiner—Patrick P. Garvin
Assistant Examiner—E. D. Irzinski
Attorney, Agent, or Firm—Robert J. Baran

[57] ABSTRACT

This invention provides novel compositions comprising aryl phosphonic or phosphinic acids substituted with more than one sulfo radical. These novel compounds may be reacted with tetravalent metal ions to provide polymers having an inorganic backbone, which polymers are useful as acid catalysts.

17 Claims, No Drawings

POLYSULFONIC ACIDS

BACKGROUND OF THE INVENTION

1. Field of the Invention

This invention provides novel compositions comprising aryl phosphonic or phosphinic acids substituted with more than one sulfo radical. These novel compounds may be reacted with tetravalent metal ions to provide polymers having an inorganic backbone, which polymers are useful as acid catalysts.

2. Description of the Art

Aromatic phosphonic acid esterification catalysts are disclosed in U.S. Pat. No. 2,776,985.

The aryl radical described in the general formula for such aromatic phosphonic acid is speculated as including a single sulfonic acid radical. There is no disclosure of compounds having more than one sulfonic acid radical or a method to prepare even the speculated mono sulfonic acid compound.

SUMMARY OF THE INVENTION

The present invention provides as a composition of matter, an aryl phosphonic or phosphinic acid comprising more than one sulfo radical covalently bonded to the aryl radical through the sulfur.

The above novel composition of matter may be reacted with a source of tetravalent metal ions to provide a polymer having an inorganic backbone and pendant sulfonic acid groups as described in International Application Number PCT/US87/00885 (International Publication Number WO87/06244) and such polymer may be used as an acid catalyst for the reactions described in said PCT application. (The PCT application is hereby incorporated by reference for its entire disclosure.)

DETAILED DESCRIPTION OF THE INVENTION

Novel and useful compounds are prepared by sulfonating aromatic phosphorus acids, e.g. phosphonic acids represented by the general formula

phosphinic acids represented by the general formula

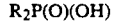

wherein R is represented by radicals having the general formula

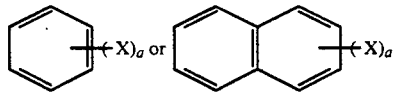

wherein X represents a halogen radical, a lower alkyl radical, a lower alkyoxy radical, a hydroxy radical, an aryl radical or an arylalkyl radical. (By lower alkyl, it is intended to mean having from 1 to about 5 carbon atoms. By aryl, it is intended to mean having up to 10 carbon atoms. By arylalkyl, it is intended to mean having up to 9 carbon atoms.) The quantity a is an integer of from 0 to 3.

The sulfonation step is carried out with a sulfonating agent, e.g. sulfur trioxide, oleum, chlorosulfonic acid, etc. The resulting sulfonated aromatic phosphorus acids have high catalytic activity, are very strong acids relative to the corresponding sulfonated aromatic compounds which are not bonded to phosphorus (due to the electron-withdrawing effect of the phosphorus groups) and are more hydrolytically and thermally stable than the corresponding ring-unsubstituted sulfonic acids.

Particular examples of suitable phosphonic or phosphinic acids include phenylphosponic acid, diphenylphosphonic acid, diphenylphosphinic acid, and diphenyldiphosphonic acid.

The sulfonation reaction may be carried out as described in "Sulfonation and Sulfation with Sulfur Trioxide", Industrial & Engineering Chemistry, Vol. 45, No. 2065, (1953), or Hohenemser, Ber., 35, 2305 (1902), which is hereby incorporated by reference. Preferably the sulfonation reaction is carried out at a temperature of from 200° C. to 300° C., for example 200° C. to 250° C. and a pressure of from ambient to super atmospheric, e.g. from about 1 to 10 atmospheres. The sulfonation reaction may be carried out for from 1 to about 20 hours, e.g. about 3 to about 17 hours. The ratio of the sulfonation agent to the aromatic phosphorus acid will be adjusted to provide at least two moles of sulfonate per mole of aromatic phosphorus acid.

The product resulting from the phenylphosphonic acid comprises 3,5 disulfonic acid phenyl phosphonic acid.

One embodiment of the present invention comprises the preparation of a reaction product of a first reactant comprising a compound of a tetravalent metal and a second reactant comprising the polysulfonic acids described above and the resulting reaction product. Preferably said polysulfonic acid is reacted in an aqueous solution with a water-soluble tetravalent metal salt to provide such reaction product. Most preferably, said tetravalent metal is zirconium. The general preparation of these reaction products may be found in U.S. Pat. Nos. 4,232,146; 4,235,990; 4,235,991; 4,256,872; 4,267,308; 4,276,409; 4,276,410; 4,276,411; 4,298,723; 4,299,943; 4,373,079; 4,384,981; 4,386,013; 4,390,690; 4,429,111; and 4,436,899 which are hereby incorporated by reference.

Another embodiment of the invention comprises a process for converting a third reactant into a resulting reaction product in the presence of an acid catalyst wherein the acid catalyst is the reaction product of a first reactant comprising a compound of a tetravalent metal and a second reactant comprising the polysulfonic acids of the present invention. In this embodiment, the third reactant and the resulting reaction product are fully described in the above PCT application.

The invention is further illustrated by the following examples which are illustrative of various aspects of the invention, and are not intended as limiting the scope of the invention as defined by the appended claims.

EXAMPLE 1

Phenyl phosphonic acid (20 g.) was carefully dissolved in 70% oleum (50 ml) and poured into a Parr bomb containing a polytetrafluoroethylene liner. The bomb was then heated for three hours at 250° C.

The reaction product was dissolved in ice water and the excess sulfate precipitated by the addition of barium hydroxide solution until no further precipitation occurred. The barium sulfate was removed by centrifugation and the product solution passed through the acid form of a strong acid ion exchange column to remove excess barium.

This solution was concentrated under reduced pressure and finally dried in a vacuum oven at 65° C. The resultant pale brown solid weighed 39.3 g.

On titration, the product showed two breaks, the ratio of the first to the second being 2.9:1. This indicates that the product was disulfonated, the first break representing two sulfo groups and one P-OH group, the second representing the second P-OH group.

The $^{31}$P NMR spectrum (D$_2$O) showed a single peak at 12.6 ppm (H$_3$PO$_4$ external standard.)

The $^{13}$C NMR spectrum (D$_2$O) showed a singlet at 127.8 ppm (C$_4$, 1 carbon), a doublet at 131.9 ppm (C$_2$ & C$_6$, 2 carbons), a doublet at 134.3 and 136.1 ppm (C$_1$, 1 carbon split by phosphorus) and a doublet at 145.6 and 145.8 ppm (C$_3$ & C$_5$, 2 carbons). These results are in good agreement with those calculated for 3, 5 disulfophenyl phosphonic acid: C1; 135.9 ppm: C2, 6; 132.4 ppm: C3, 5; 144.7 ppm: C4, 127.1 ppm.

EXAMPLE 2

Sulfur trioxide (158 parts) was distilled onto phenyl phosphonic acid (150 parts), the addition taking about 1 hour. The mixture was heated for 1 hour at 200° C., and for 17 hours at 250° C. $^{13}$C NMR analysis of the product showed that it contained disulfophenl phosphonic acid and monosulfophenyl phosphonic acid in the ratio of 85:15.

EXAMPLE 3

Diphenyl-4, 4'-diphosphonic acid (10 g) was dissolved in 70% oleum (25 ml) and heated and worked up according to the method of Example 1. The product was a yellow solid (8.9 g). Its titration curve showed two breaks in the ratio of 1.8:1, indicating a disulfonated product, disulfodiphenyldiphosphonic acid.

EXAMPLE 4

The product of Example 1 was stored as an aqueous solution, 68.2 wt. % disulfophenylphosponic acid. A quantity 71.4 g of this solution was diluted in 750 ml distilled H$_2$O and brought to reflux. A second solution, containing 24.65 g ZrOCl$_2$.8H$_2$O in 750 ml H$_2$O was added to the first solution, and the whole quantity refluxed for two hours. Approximately two thirds of the water in this solution was removed by distillation, and the remainder by rotovap. This material was dried in vacuo at 110° C. until a constant weight was achieved. 58.0 dry solid was recovered. Elemental analysis and titration was consistent with the compound Zr(O$_3$PC$_6$H$_3$(SO$_3$H)$_2$)$_2$. $^{31}$P NMR showed a single peak at -8.8 ppm (H$_3$PO$_4$ referenced at 0 ppm), consistent with the compound Zr(O$_3$PC$_6$H$_3$(SO$_3$H)$_2$)$_2$.

While particular emodiments of the invention have been described, it will be understood, of course, that the invention is not limited thereto since many obvious modifications can be made and it is intended to include within this invention any such modifications as will fall within the scope of the appended claims.

What is claimed is:

1. As a composition of matter, an aryl phosphonic or phosphonic or phosphinic acid comprising more than one sulfo radical covalently bonded to the aryl radical through the sulfur wherein said aryl radical has the general formula

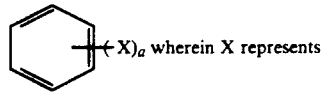

a halogen radical, a lower alkyl radical, a lower alkoxy radical, a hydroxy radical, an aryl radical or an aryl alkyl radical and a is an integer of from 0 to 3.

2. The composition of claim 1 wherein said sulfo radical comprises a sulfonic acid radical.

3. The composition of claim 2 wherein said composition comprises from 2 to 5 sulfonic acid radicals.

4. The compositions of claim 1 wherein the aryl radical selected from the group consisting of phenyl and biphenyl radicals.

5. The compositions of claim 4 wherein said aryl acid is selected from the group consisting of phenylphosphonic acid and biphenyl diphosphonic acid.

6. The compositions of claim 4 wherein said aryl acid is diphenylphosphinic acid.

7. The compositions of claim 1 wherein said composition is a disulfonic acid.

8. The compositions according to claim 7 wherein said aryl radical is phenyl.

9. A composition according to claim 8 wherein said aryl acid is phenylphosphonic acid.

10. The composition of claim 3 wherein said aryl acid comprises four sulfonic acid radicals.

11. The composition of claim 10 wherein said aryl acid is selected form the group consisting of biphenylphosphonic acid and diphenylphosphinic acid.

12. The reaction product of a first reactant comprising a tetravalent metal ion and a second reactant comprising the composition of claim 1.

13. The reaction product of claim 12 wherein said first reactant is a tetravalent metal salt.

14. The reaction product of claim 13 wherein said tetravalent metal is selected from the group consisting of Zr, U, Ti, Th, Sn, Pb, Ce and mixtures thereof.

15. The reaction product of claim 14 wherein said tetravalent metal is Zr.

16. The reaction product of claim 15 wherein said second reactant is 3, 5 disulfonic acid phenylphosphonic acid.

17. In a process for coverting a third reactant into a resulting reaction product in the presence of an acid catalyst the improvement comprising providing, as said acid catalyst, the reaction product of claim 12.

* * * * *